United States Patent
Ferraro et al.

(10) Patent No.: US 10,048,231 B2
(45) Date of Patent: Aug. 14, 2018

(54) APPARATUS FOR DETERMINING AND/OR MONITORING AT LEAST ONE PROCESS VARIABLE

(71) Applicant: Endress + Hauser GmbH + Co. KG, Maulburg (DE)

(72) Inventors: Franco Ferraro, Schworstadt (DE); Philipp Walser, Eimeldingen (DE)

(73) Assignee: ENDRESS + HAUSER GMBH + CO. KG, Maulburg (DE)

( * ) Notice: Subject to any disclaimer, the term of this patent is extended or adjusted under 35 U.S.C. 154(b) by 662 days.

(21) Appl. No.: 14/364,105

(22) PCT Filed: Nov. 22, 2012

(86) PCT No.: PCT/EP2012/073320
§ 371 (c)(1),
(2) Date: Jun. 10, 2014

(87) PCT Pub. No.: WO2013/087389
PCT Pub. Date: Jun. 20, 2013

(65) Prior Publication Data
US 2014/0373632 A1    Dec. 25, 2014

(30) Foreign Application Priority Data

Dec. 13, 2011   (DE) .................. 10 2011 088 351

(51) Int. Cl.
*G01N 29/22* (2006.01)
*G01F 25/00* (2006.01)
(Continued)

(52) U.S. Cl.
CPC ......... *G01N 29/22* (2013.01); *G01F 23/0076* (2013.01); *G01F 23/296* (2013.01);
(Continued)

(58) Field of Classification Search
CPC ..................................................... G01N 29/22
(Continued)

(56) References Cited

U.S. PATENT DOCUMENTS 4,353,245 A * 10/1982 Nicolai ............... G01M 3/3245
340/605
5,774,378 A * 6/1998 Yang ..................... G01F 1/8436
702/104
(Continued)

FOREIGN PATENT DOCUMENTS

CN    101371523 A    2/2009
CN    101535770 A    9/2009
(Continued)

OTHER PUBLICATIONS

International Search Report, EPO, The Netherlands, dated Mar. 6, 2013.
(Continued)

*Primary Examiner* — Hezron E Williams
*Assistant Examiner* — Tarun Sinha
(74) *Attorney, Agent, or Firm* — Bacon & Thomas, PLLC

(57) ABSTRACT

Apparatus (1) for determining and/or monitoring at least one process variable, comprising: a primary side (I) and a secondary side (II), which are galvanically isolated from one another, wherein the secondary side (II) has a sensor element sensitive for the process variable (2) and an electronics unit (9) of the secondary side and provides a measurement signal representing the process variable, and wherein the primary side (I) has an electronics unit (8) of the primary side for evaluating the measurement signal and for producing an output signal. The apparatus (1) is distinguished by features including that the electronics unit (9) of the secondary side has a modulation unit (14), which produces a modulated measurement signal by at least at times modulating at least (Continued)

one other piece of information onto the measurement signal representing the process variable, and that the electronics unit (9) of the secondary side transmits the modulated measurement signal via a galvanically isolated interface to the primary side (I).

10 Claims, 1 Drawing Sheet

(51) Int. Cl.
*G01N 9/00* (2006.01)
*G01N 11/10* (2006.01)
*G01F 23/00* (2006.01)
*G01N 29/02* (2006.01)
*G01F 23/296* (2006.01)

(52) U.S. Cl.
CPC ......... *G01F 25/0076* (2013.01); *G01N 9/002* (2013.01); *G01N 11/10* (2013.01); *G01N 29/02* (2013.01); *G01F 23/2967* (2013.01); *G01N 2291/02818* (2013.01); *G01N 2291/02836* (2013.01)

(58) Field of Classification Search
USPC .......................................................... 73/658
See application file for complete search history.

(56) References Cited

U.S. PATENT DOCUMENTS

| | | | |
|---|---|---|---|
| 7,778,185 B2 | 8/2010 | Kollner et al. | |
| 8,354,941 B2 | 1/2013 | Wernet | |
| 8,381,600 B2 | 2/2013 | Huber | |
| 8,423,321 B2 | 4/2013 | Gaiser | |
| 8,898,036 B2 | 11/2014 | Sittler et al. | |
| 2003/0011768 A1* | 1/2003 | Jung | A61B 5/0088 356/326 |
| 2005/0140522 A1* | 6/2005 | Heilig | G01F 23/296 340/870.01 |
| 2010/0132454 A1* | 6/2010 | Wernet | G08C 19/02 73/304 R |
| 2012/0174671 A1 | 7/2012 | Urban | |

FOREIGN PATENT DOCUMENTS

| | | |
|---|---|---|
| CN | 101772745 A | 7/2010 |
| DE | 102005036409 A1 | 2/2007 |
| DE | 102006030962 A1 | 1/2008 |
| DE | 102006051900 A1 | 5/2008 |
| DE | 102008033336 A1 | 1/2010 |
| DE | 102009012474 A1 | 9/2010 |
| EP | 2182331 A1 | 5/2010 |
| WO | 03021839 A2 | 3/2003 |
| WO | 2008003629 A1 | 1/2008 |
| WO | 2011038985 A1 | 4/2011 |

OTHER PUBLICATIONS

English Translation of the International Preliminary Report on Patentability, WIPO, Geneva, dated Jun. 26, 2014.
German Search Report, German PTO, Munich, dated Jul. 26, 2012.
Modulation (Technik) Nov. 27, 2011, Wikipedia (document in German language, a machine translation to English of p. 1 is provided.

* cited by examiner

APPARATUS FOR DETERMINING AND/OR MONITORING AT LEAST ONE PROCESS VARIABLE

TECHNICAL FIELD

The present invention relates to an apparatus for determining and/or monitoring at least one process variable, wherein the apparatus has a primary side and a secondary side, which are galvanically isolated from one another, wherein the secondary side has a sensor element sensitive for the process variable and a secondary side electronics unit and provides a measurement signal representing the process variable, and wherein the primary side has a primary side electronics unit for evaluating the measurement signal and for producing an output signal. The process variable is, for example, the fill level of a liquid or a bulk good in a container, the density, the viscosity, the electrical conductivity, the flow or the pH-value of a liquid.

BACKGROUND DISCUSSION

Known from the state of the art are a large number of measuring devices, which are equipped with two electronic units, which are often galvanically isolated from one another. The primary side electronics unit is connected with the energy supply of the measuring device, while the secondary side electronics unit is associated with the sensor. Provided for energy and data transmission are one or more galvanically isolated interfaces, which can be embodied inductively or capacitively. Communication between the two electronic units occurs, for example, from the primary side to the secondary side via frequency modulation and in the reverse direction via load modulation, such as is described in DE 10 2006 051 900 A1. Also, it is known to use amplitude modulation. Often, no, or only a unidirectional, communication occurs from the primary side to the secondary side via the galvanically isolated interface and an optocoupler serves for data transmission from the secondary side to the primary side.

As a rule, the secondary side transmits to the primary side measurement data, which represent the process variable, while from the primary side to the secondary side, above all, parameter data or sensor-specific, identifying data are transmitted. Based on space, energy and cost, the number of interfaces between primary side and secondary side is, as a rule, reduced to a minimum. In this way, the transmissible information is strongly limited.

SUMMARY OF THE INVENTION

An object of the invention is to provide an apparatus for determining at least one process variable, in the case of which apparatus information exchange between primary side and secondary side is improved.

The object is achieved by a pipeline or a container, comprising: a primary side and a secondary side, which are galvanically isolated from one another, said secondary side has a sensor element sensitive for the process variable and an electronics unit of said secondary side, and provides a measurement signal representing the process variable; and the primary side has an electronics unit of the primary side for evaluating the measurement signal and for producing an output signal, wherein: said electronics unit of said secondary side includes a modulation unit, which produces a modulated measurement signal by at least at times modulating at least one other piece of information onto the measurement signal representing the process variable; and said electronics unit of the secondary side transmits the modulated measurement signal via a galvanically isolated interface to the primary side.

The secondary side of the measuring device associated with the sensor element produces the measurement signal, which the primary side evaluates with reference to the process-variable. According to the invention, the electronics unit of the secondary side includes a modulation unit, which produces a modulated measurement signal by at least at times modulating at least one other piece of information onto the measurement signal representing the process variable. The electronics unit of the secondary side transmits this modulated measurement signal via a galvanically isolated interface to the primary side. By evaluating the modulation of the measurement signal, the primary side, thus, acquires more information than in the case of transmission of just the measurement signal. Proceeding based on the evaluated modulated measurement signal, the primary side produces an output signal, which displays a current value of the process variable or an error state and is suppliable, for example, to a control room or to field devices downstream from the apparatus. The output signal can be, for example, a usual 4-mA signal and differs from the modulated measurement signal, which is a signal internal to the measuring device.

In an embodiment, the modulation unit performs a frequency modulation or a pulse width modulation. The measurement signal is, as a rule, an electrical, alternating voltage signal. The modulated measurement signal possesses, compared with the measurement signal, corresponding to the embodiment of the modulation unit, at least at times a changed frequency or a changed pulse-pause ratio.

The at least one other piece of information can be, for example, information concerning a configuration of the sensor element or the secondary side electronics unit, information for determining or monitoring an additional process variable, or information concerning a current operating state of the secondary side. The primary side can check whether data transmitted from it arrived correctly at the secondary side, e.g. whether the configuration of the electronics unit of the secondary side is correct. For the case, in which the configuration is performed directly at the secondary side, the primary side learns, via the modulation of the measurement signal, how the secondary side is configured. Furthermore, by regular transmission to the primary side of parameters set on the secondary side, a control function is enabled relative to parameters changed due to an error during operation of the measuring device. This read back function relative to the configuration increases the safety of the apparatus.

In an embodiment, the secondary side shows, via the current operating state, whether the electronics unit of the secondary side is located in measurement operation for determining and/or monitoring the process variable or in a diagnostic state. The terminology diagnostic state means a state performing diagnostics for discovering defects in components of the electronics unit of the secondary side and in components of the sensor element.

In an embodiment, the electronics unit of the primary side determines, based on the frequency of the modulated measurement signal, a current value of the process variable and registers the other information based on the pulse width of the modulated measurement signal.

In an additional embodiment, the electronics unit of the primary side determines, based on the frequency of the modulated measurement signal, a current value of the process variable and registers furthermore, likewise based on frequency, the other information.

In an embodiment of the invention, wherein the apparatus is a vibronic measuring device, which has a mechanically oscillatable unit and a driving/receiving unit, wherein the driving/receiving unit excites the mechanically oscillatable unit by means of a transmitted signal to execute mechanical oscillations and receives oscillations from the mechanically oscillatable unit and transduces such into an electrical, received signal, the modulated measurement signal bears information concerning at least one oscillatory characteristic.

In an embodiment of the vibronic measuring device, the other information relates to the embodiment of the driving/receiving unit or the embodiment of the apparatus as a limit level switch for a minimum or a maximum limit-level or to an oscillatory characteristic or to a variable for evaluating the quality of the oscillatable unit and/or the driving/receiving unit.

An embodiment provides that the measurement signal bears the frequency of the oscillations and that the other information is the amplitude, the phase shift between the transmitted signal and the received signal, or an energy requirement, especially an electrical current requirement, of the driving/receiving unit. From the frequency of the oscillation, the primary side determines the process variable, fill level. A change of phase shift indicates, for example, a viscosity change of the medium. If the medium falls below the oscillatable unit or the oscillation excitement occurs outside a frequency range, in which the oscillation characteristics depend on the process medium, detection of accretion is possible. A decrease in the amplitude compared with the amplitude of oscillation of an accretion free oscillatable unit suggests accretion formation. The quality of the oscillatable unit and of the driving/receiving unit is determinable via the energy requirement.

The process variable is preferably the fill level, the density and/or the viscosity of a medium. This is true especially for the case, in which the apparatus is a vibronic measuring device. The process variable can be, however, any other process variable, such as, for example, pressure, temperature, flow or pH-value.

BRIEF DESCRIPTION OF THE DRAWINGS

The invention will now be explained in greater detail, based on the appended drawing, the figures of which show as follows.

DETAILED DISCUSSION IN CONJUNCTION WITH THE DRAWINGS

Figure 1:
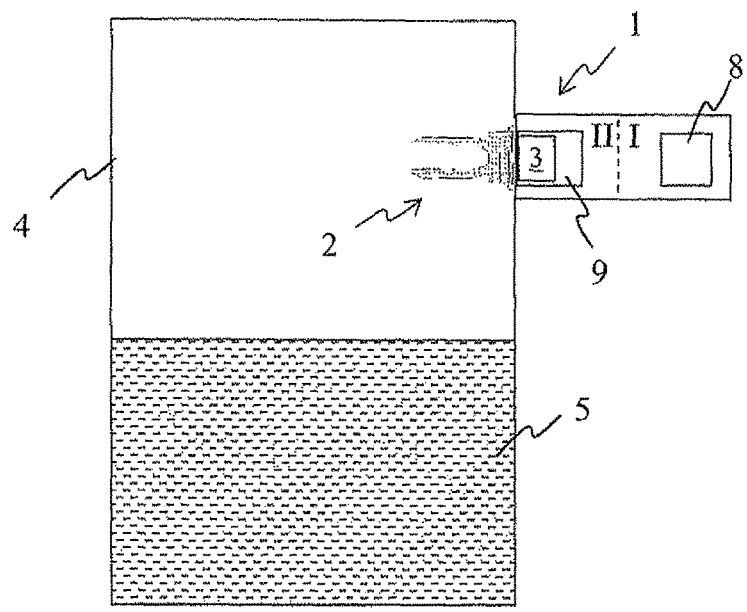
FIG. 1 is a measuring device in use.

FIG. 1 shows a vibronic measuring device 1 for determining and/or monitoring limit level, density, or viscosity of a medium 5 in a container 4. The measuring device 1 is arranged at a height in the container 4 corresponding to a limit level to be monitored. The reaching of the limit level is detected based on a covering of the sensor unit, which is present in the form of a mechanically oscillatable unit 2. In the illustrated case, the measuring device 1 serves as an overfilling preventer and monitors whether the medium 5 has achieved the limit level. If this is the case, the measuring device 1 produces a "covered" report.

A driving/receiving unit 3 excites the oscillatable unit 2 to execute mechanical oscillations, for example, mechanical oscillations with the resonant frequency. Preferably, the driving/receiving unit 3 is embodied as an electromechanical transducer unit having one or more piezoelectric elements, which also receive the oscillations of the oscillatable unit 2 and transduce them into electrical signals. If the oscillatable unit 2 is covered with medium 5, the oscillation frequency changes compared to oscillation with an uncovered oscillatable unit 2. By means of a frequency evaluation, thus, the limit level is monitorable. Determinable from the oscillation characteristics are furthermore the density and the viscosity of the medium surrounding the oscillatable unit 2.

For reasons of electromagnetic compatibility and, for example, also, in order to be applicable in explosion protected regions, the measuring device 1 uses galvanic isolation between a secondary side II having the oscillatable unit 2 and electronic components assembled into an electronics unit 9 of the secondary side required for capturing the measurement signal, and a primary side I having a connector for energy supply of the measuring device 1 and a primary side electronics unit 8 for evaluating the measurement signal as regards the process variable. The secondary side II transmits the measurement signal to the primary side I, which evaluates the measurement signal and produces the output signal of the measuring device 1.

The invention will now be explained in greater detail based on a vibronic fill level measuring device. In principle however, the invention is applicable in any measuring devices having galvanic isolation, in the case of which the secondary side produces the measurement signal and the primary side receives the measurement signal from the secondary side for evaluation.

Figure 2:
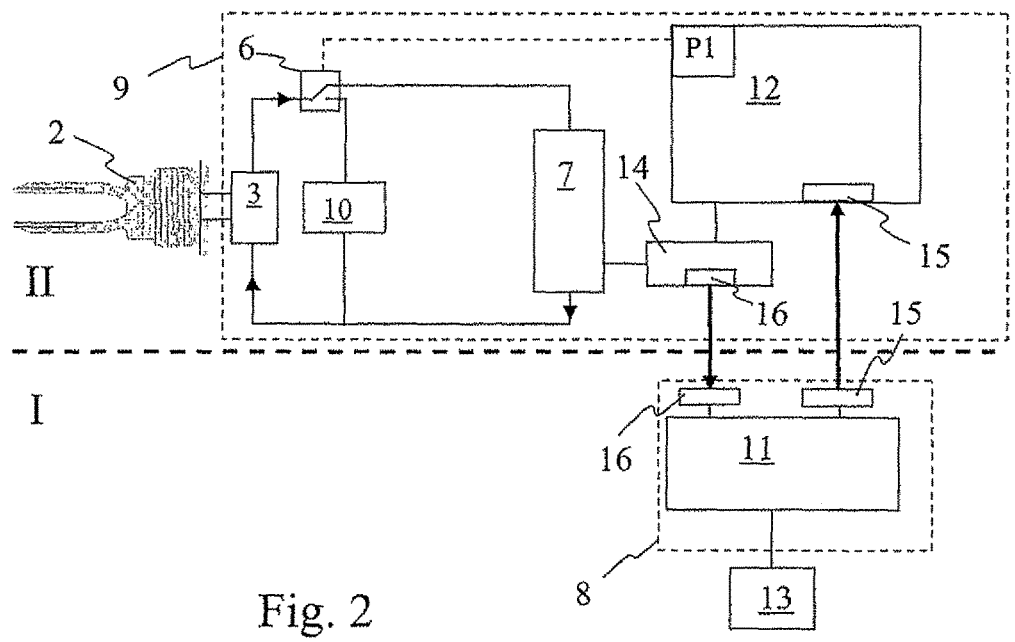
FIG. 2 is a schematic, block diagram of the measuring device of FIG. 1.

FIG. 2 shows a schematic representation of the construction of a vibronic measuring device 1 such as the one shown in FIG. 1. Sensor unit 2 is associated with a secondary side II, while the voltage source 13 for energy supply of the measuring device 1 is associated with a primary side I. Primary side I and secondary side II are galvanically isolated from one another. Via a galvanically isolated interface 15, which can be, for example, an inductive or capacitive interface, the electronics unit 8 of the primary side transmits energy and data to the secondary side II. Energy and data can also be transmitted via separate interfaces. The data transmission occurs, in such case, unidirectionally from the primary side I to the secondary side II. There are also options for embodiments, in which the primary side I transmits no data to the secondary side II, for example, in case a memory element of the electronics unit 9 of the secondary side is directly configurable and, thus, the secondary side has all information for configuration of the oscillatory circuit for oscillatory excitement of the oscillatable unit 2.

The electronics unit 8 of the primary side includes a logic unit in the form of a first microcontroller 11. The electronics unit 9 of the secondary side likewise includes a logic unit in the form of a second microcontroller 12. Instead of microcontrollers 11, 12, also other intelligent logic units can be used, for example, an ASIC or an FPGA. Usable on the secondary side is, in principle, also an I/O controller or a bus communication controlled, remote I/O expander.

The driving/receiving unit 3, which excites the mechanically oscillatable unit 2 to execute mechanical oscillations and receives the oscillations from the mechanically oscillatable unit 2, is integrated into an electrical, oscillatory circuit. The electronic components of the oscillatory circuit are known sufficiently to those skilled in the art and are shown here combined into the processing unit 7 for better overview. The electronic components include, for example, filter, amplifier, phase shifter and the like.

The second microcontroller 12 controls the processing unit 7 and sets parameters for oscillation excitement according to a desired configuration. This configuration is sent to the second microcontroller 12 from the first microcontroller 11. For example, the configuration in the case of a measuring device 1 installed for detection of a maximum fill level differs from that of a measuring device 1 installed for detection of a minimum fill level. Furthermore, differences arise, depending on the embodiment of the driving/receiving unit 3.

Communication between electronics unit 8 of the primary side and electronics unit 9 of the secondary side via the interface occurs unidirectionally from the primary side I to the secondary side II. For this, the first microcontroller 11 sends, per serial communication, a signal to the second microcontroller 12. This signal includes configuration data. The second microcontroller 12 configures the oscillatory circuit with these data. For example, it sets parameters of filters or amplifiers in the oscillatory circuit, respectively controls switches for selection of certain possible signal paths, or it establishes the value for the phase shift between transmitted and received signal of the driving/receiving unit 3. The measurement signal is coupled out from the oscillatory circuit and is present in the form of an electrical, alternating voltage, whose frequency bears information concerning whether the oscillatable unit 2 is covered. The measurement signal is fed to a modulation unit 14, which is controlled by the second microcontroller 12. The modulation unit 14 can also be embodied as part of the second microcontroller 12.

The second microcontroller 12 controls the modulation unit 14 in such a manner that it alters the measurement signal as a function of the information to be impressed on the measurement signal. In an embodiment, the modulation unit 14 alters the frequency of the measurement signal. In another, alternative or additional embodiment, the modulation unit 14 varies the pulse-pause ratio. The modulation unit 14 leads the modulated measurement signal via another galvanically isolated interface to the primary side I for evaluation. In a digital embodiment, an analog digital converter on the primary side receives the modulated measurement signal and converts it into a digital measurement signal, which the first microcontroller 11 evaluates. An at least partially analog measurement signal processing is, however, likewise possible.

The electronics unit 8 of the primary side evaluates the measurement signal in reference to the frequency, in order to detect the covered state of the oscillatable unit 2. For this, for example, a limit value is furnished for the frequency, whose subceeding is associated with the covered state and whose exceeding is associated with the free state. By comparing the measured frequency with the furnished frequency, it is accordingly recognizable whether the limit level to be monitored has been reached or not. The electronics unit 8 of the primary side produces an output signal dependent on the fill level, for example, an output signal in the form of a 4-20 mA signal. This output signal is suppliable to a process monitoring unit in a control room or to following process devices.

Besides the process variable, the electronics unit 8 of the primary side ascertains, according to the invention, additional information from the modulated measurement signal. The modulation unit 14 can also modulate the measurement signal in different ways, so that different information are transmittable one after the other via the modulated measurement signal to the primary side I. The modulation can, in such case, occur continuously or in certain intervals, preferably in periodic intervals. Examples of information, which can be relevant for the primary side I and transmittable via the modulated measurement signal, are given below.

The electronics unit 8 of the primary side ascertains the fill level based on the frequency of the transmitted modulated measurement signal. The information modulated on can be reflected, for example, by another oscillatory characteristic of the oscillatable unit, such as the amplitude or the phase shift between transmitted signal and received signal. From this, information concerning density and/or viscosity of the medium can be provided. Accretion on the oscillatable unit 2 is detectable based on a lessened amplitude at the frequency accompanying a freely oscillating oscillatable unit 2.

Present in the oscillatory circuit is a switch 6 controllable by the second microcontroller 12. For output of the control signal for the switch 6, the second microcontroller 12 possesses a control output P1. The connection of the control output P1 with the switch 6 is indicated via the dashed line. By means of the switch 6, instead of the mechanically oscillatable unit 2, an RC-unit is introducible into the oscillatory circuit. The signal received at the RC-unit no longer contains information concerning the process variable. The oscillation occurs, in this case, correspondingly, also not with the resonant frequency of the oscillatable unit 2, but, instead, with a tear-off frequency predetermined by the components of the electronics unit 9 of the secondary side. In this state, the second microcontroller 12 conducts a diagnosis of the electronic components of the oscillatory circuit. Preferably, the second microcontroller 12 conducts diagnoses at regular intervals.

The tear-off frequency can be present not only during the diagnostic state, but, instead, also during measurement operation, when the damping of the oscillations of the oscillatable unit 2 is so great, for example, due to accretion or high viscosity, that the oscillatable unit 2 no longer executes mechanical oscillations. Also, when a cable break is present and the oscillatable unit 2 because of this no longer is excitable to execute oscillations, the oscillatory circuit oscillates with the tear-off frequency. If the primary side I evaluates the frequency of the transmitted measurement signal \ and detects the tear-off frequency, then it produces an alarm signal or an output signal corresponding to the safe state. The safe state is, for example, in the case of a limit level switch for an overfilling preventer, i.e. for detection of the reaching of a maximum fill level, the covered state.

In order that the secondary side II can perform diagnoses independently of command from the primary side I and it is nevertheless known on the primary side I that a diagnosis is being performed and the measured frequency of the measurement signal represents no oscillation frequency in the case of excited oscillatable unit 2, the secondary side II transmits this information to the primary side I. For this, the second microcontroller 12 controls the modulation unit 14 in such a manner that the modulation unit 14 always changes the frequency, or the pulse-pause ratio, of the present measurement signal, when a diagnosis is being performed. In the case of a frequency modulation, this leads especially to a frequency shift of the tear-off frequency, with which the oscillatory circuit oscillates in the diagnostic state. If the electronics unit 8 of the primary side detects the correspondingly shifted frequency, respectively the changed pulse-pause ratio, it evaluates the transmitted modulated measurement signal not with reference to the process variable, or at least produces no corresponding output signal, but, instead, keeps the output signal produced before the diagnosis. In this way, it is prevented that the primary side I, due to detection of the tear-off frequency, produces a false alarm. Since the secondary side II starts the diagnosis independently, no transmission of a diagnosis starting signal is required from the primary side I to the secondary side II, so that the interface 15 does not have to be activated for this. This saves energy.

Concretely, in the case of a limit level switch for monitoring a maximum fill level, i.e. in the "maximum" configuration, there exists for the frequency then four different ranges: A first range, which accompanies an uncovered sensor unit 2 and indicates a normal state of the measuring device 1; a second range, which accompanies a covered sensor unit 2 and leads to change of the output signal of the measuring device 1, since the limit level to be monitored has been achieved; a third range, which lies outside of the first and second ranges and includes at least one tear-off frequency, which occurs in the case of a defect and leads to output of an alarm signal; and a fourth range, which is achieved by modulation of the measurement signal and includes at least one frequency, which is, for example, a multiple of the tear-off frequency and indicates the diagnostic state.

In the yet to be published German patent application DE 102010039585.4 (US 20130139585), a method for compensation of coupling effects in the piezoelectric elements of the transducer unit of a vibronic measuring device is described, which permits, also in high viscosity media, maintaining excitation at the resonant frequency. Whether currently a compensation is being performed or not represents likewise information, which can be modulated onto the measurement signal.

Other information transmittable with the measurement signal to the primary side I is information relative to the configuration of the measuring device 1. Such information is provided by the electronics unit 8 of the primary side to the electronics unit of the secondary side 9, as a rule, at start-up of the measuring device 1. Since this information can then be read-out from the electronics unit 9 of the secondary side and transmitted to the primary side I, an opportunity is provided for checking whether a wrong configuration is present. The wrong configuration can, in such case, occur from the beginning or during operation of the measuring device 1, so that the obtaining of information concerning the current configuration is appropriate not only directly after start-up of the measuring device 1, but, instead, also in the on-going operation of the measuring device 1.

Another modulatable information is the energy requirement of the driving/receiving unit 3. Especially, the secondary side II determines the electrical current, which is required for exciting the oscillatable unit 2 to resonant oscillations via the oscillatory circuit, and the secondary side II transmits the electrical current value via the modulation to the primary side I. The primary side microcontroller 11 ascertains from this information the quality of the oscillatory circuit, respectively the quality of the driving/receiving unit 3 and oscillatable unit 2. A lessened quality happens, for example, in the case of accretion formation on the oscillatable unit 2 and leads to a lessened accuracy of measurement. In some cases, especially in the case of monitoring a process variable by comparison with a predetermined limit value, even an incorrect statement concerning the process variable is possible. By evaluating the information concerning the energy requirement, such an incorrect statement can be prevented.

The modulation unit 14 can also be embodied in such a manner and the modulation of the second microcontroller 12 controlled in such a manner that different information is modulated onto the measurement signal via different pulse-pause ratios or different frequencies. It is likewise possible to transmit different information by the same pulse-pause ratio by predetermining a start signal for the data transmission and a fixed sequence of the information.

The invention claimed is:

1. An apparatus for determining and/or monitoring at least one process variable of a medium in a pipeline or a container, comprising:
a primary side and a secondary side, which are galvanically isolated from one another, said secondary side has a sensor element sensitive for the process variable and an electronics unit of said secondary side, and provides a measurement signal representing the process variable; and
the primary side has an electronics unit of the primary side for evaluating the measurement signal and for producing an output signal, wherein:
said electronics unit of said secondary side includes a modulation unit, which produces a modulated measurement signal by at least at times modulating at least one other piece of information onto the measurement signal representing the process variable; and
said electronics unit of the secondary side transmits the modulated measurement signal via a galvanically isolated interface to the primary side.

2. The apparatus as claimed in claim 1, wherein:
modulation unit is embodied to perform a frequency modulation or a pulse width modulation.

3. The apparatus as claimed in claim 1, wherein:
said at least one other piece of information relates to information concerning a configuration of said sensor element or said electronics unit of the secondary side, information for determining or monitoring an additional process variable, or information concerning a current operating state of said secondary side.

4. The apparatus as claimed in claim 3, wherein:
said secondary side electronics shows, via the current operating state, whether said electronics unit of the secondary side is located in measurement operation for determining and/or monitoring the process variable or in a diagnostic stale.

5. The apparatus as claimed in claim 2, wherein:
said electronics unit of the primary side determines, based on frequency of the modulated measurement signal, a current value of the process variable and registers the other information based on pulse width of the modulated measurement signal.

6. The apparatus as claimed in claim 2, wherein:
said electronics unit of the primary side determines, based on frequency of the modulated measurement signal, a current value of the process variable and registers the other information.

7. The apparatus as claimed in claim 1, wherein:
the apparatus is a vibronic measuring device, which has a mechanically oscillatable unit and a driving/receiving unit;
said driving/receiving unit excites said mechanically oscillatable unit by means of a transmitted signal to execute mechanical oscillations and receives oscillations from said mechanically oscillatable unit and transduces such into an electrical, received signal, and the modulated measurement signal bears information concerning at least one oscillatory characteristic.

8. The apparatus as claimed in claim 7, wherein:
other information relates to the embodiment of said driving/receiving unit or the embodiment of the apparatus as a limit level switch for a minimum or a maximum limit level or to an oscillatory characteristic or to a variable for evaluating the quality of said oscillatable unit and said driving/receiving unit.

9. The apparatus as claimed in claim 7, wherein:
the measurement signal bears the frequency of the oscillations and the other information is the amplitude, the phase shift between the transmitted signal and the received signal, or an energy requirement, especially an electrical current requirement, of said driving/receiving unit.

10. The apparatus as claimed in claim 1, wherein:
the process variable is the fill level, the density and/or the viscosity of the medium.

* * * * *